United States Patent [19]

Mueller

[11] Patent Number: 4,912,248

[45] Date of Patent: Mar. 27, 1990

[54] NOVEL ANTI-INFLAMMATORY AGENTS, PHARMACEUTICAL COMPOSITIONS AND METHODS FOR REDUCING INFLAMMATION

[75] Inventor: Larry G. Mueller, Oxford, Ohio

[73] Assignee: The Procter & Gamble Company, Cincinnati, Ohio

[21] Appl. No.: 206,966

[22] Filed: Jun. 8, 1988

Related U.S. Application Data

[63] Continuation of Ser. No. 51,446, May 18, 1987, abandoned.

[51] Int. Cl.$^4$ .............................................. C07C 69/76
[52] U.S. Cl. ...................................... 560/56; 560/254
[58] Field of Search ................ 560/56, 254; 514/532, 514/541

[56] References Cited

U.S. PATENT DOCUMENTS

| | | | |
|---|---|---|---|
| 3,562,336 | 2/1971 | Nelson | 260/613 |
| 3,637,767 | 1/1972 | Alvarez | 260/348 |
| 3,641,161 | 2/1972 | Fried et al. | 260/613 D |
| 3,686,238 | 8/1972 | Zaffaroni | 260/399 |
| 3,787,580 | 1/1974 | Fried et al. | 424/308 |
| 3,792,167 | 2/1974 | Fried et al. | 424/337 |
| 3,896,157 | 7/1975 | Fried et al. | 260/469 |
| 3,958,012 | 5/1976 | Fried et al. | 424/333 |
| 4,328,356 | 5/1982 | Giordano et al. | 560/56 |
| 4,605,758 | 8/1986 | Schloemer | 560/56 |
| 4,661,628 | 4/1987 | Cannata et al. | 560/56 |
| 4,665,224 | 5/1987 | Mora | 560/56 |

FOREIGN PATENT DOCUMENTS

| | | |
|---|---|---|
| 903569 | 2/1986 | Belgium . |
| 35305 | 9/1981 | European Pat. Off. ............. 560/56 |
| 89711 | 9/1983 | European Pat. Off. ............. 560/56 |
| 112130 | 6/1984 | European Pat. Off. . |
| 158255 | 10/1985 | European Pat. Off. . |
| 166135 | 1/1986 | European Pat. Off. ............. 560/56 |
| 0227078 | 1/1987 | European Pat. Off. . |
| 53-82761 | 7/1978 | Japan . |
| 1297306 | 11/1972 | United Kingdom . |
| 2050363 | 1/1981 | United Kingdom . |

OTHER PUBLICATIONS

Harrison, I., et al., "Nonsteroidal Anti-Inflammatory Agents, I., 6-Substituted 2-Naphthylacetic Acids", *Journal of Medicinal Chemistry*, vol. 13 (1970), pp. 203-205.

*Primary Examiner*—Paul J. Killos
*Attorney, Agent, or Firm*—Milton B. Graff, IV; Kim William Zerby; Jack D. Schaeffer

[57] ABSTRACT

Compounds and diastereomeric mixtures of specific 2-naphthyl-containing ester compounds, especially naproxen ester and naproxol ester compounds, having two or more chiral centers. These compounds are effective as anti-inflammatory agents, analgesic agents, and/or antipyretic agents. They are readily absorbed as the diastereomeric mixture, especially through the skin following topical application.

18 Claims, No Drawings

NOVEL ANTI-INFLAMMATORY AGENTS, PHARMACEUTICAL COMPOSITIONS AND METHODS FOR REDUCING INFLAMMATION

This is a continuation of application Ser. No. 051,446, filed on May 18, 1987.

BACKGROUND OF THE INVENTION

The present invention relates to compounds and diastereomeric mixtures of naproxen esters or naproxol esters. Diastereomeric mixtures of these esters are more readily absorbed by humans or lower animals, especially through the skin when applied topically, than naproxen or ester derivatives which are not diastereomeric mixtures. The present invention also relates to pharmaceutical compositions, especially pharmaceutical compositions in a form suitable for topical delivery, containing a diastereomeric mixture of a naproxen ester or naproxol ester. The present invention finally relates to methods for treating or preventing inflammation in humans or lower animals by administering, especially topically to skin, a diastereomeric ester mixture or a pharmaceutical composition of the present invention.

The search for new non-steroidal anti-inflammatory ("NSAI") drugs over the past ten to twenty years has led to the testing by various researchers and companies of thousands of compounds for efficacy as anti-inflammatory agents. One compound which has been identified as being a good NSAI drug is (S)-2-(6-methoxy-2-naphthyl)propionic acid, commonly referred to as "naproxen". Naproxen and various derivatives of naproxen (e.g., the alcohol (i.e., "naproxol") and aldehyde derivatives, and certain esters of naproxen) have been shown to have anti-inflammatory activity when administered orally. Such disclosures are contained, for example, in Harrison et al., "Nonsteroidal Anti-inflammatory Agents. I. 6-Substituted 2-Naphthylacetic Acids", *J. Med. Chem.*, 13, pages 203-205 (1970); U.S. Pat. No. 3,641,161, to Fried et al., issued Feb. 8, 1972; U.S. Pat. No. 3,792,167, to Fried et al., issued Feb. 12, 1974; U.S. Pat. No. 3,562,336, to Nelson, issued Feb. 9, 1971; Great Britain Patent Specification No. 1,297,306, to Syntex Corporation, published Nov. 22, 1972; U.S. Pat. No. 3,958,012, to Fried et al., issued May 18, 1976; U.S. Pat. No. 3,637,767, to Alvarez, issued Jan. 25, 1972; and U.S. Pat. No. 3,896,157, to Fried et al., issued July 22, 1975; the disclosures of all of these publications being incorporated herein by reference in their entirety. Straight chain fatty acid esters of the alcohol derivative of naproxen ("naproxol esters") have been disclosed in Great Britain Patent Specification No. 2,050,363, published Jan. 7, 1981 by Del Bono, the disclosures of which are incorporated by reference herein in their entirety. Phenyl ring-containing esters of naproxen and naproxol have also been disclosed, for example, in U.S. Pat. No. 3,787,580, to Fried et al., issued Jan. 22, 1974, the disclosures of which are incorporated by reference herein in their entirety.

Furthermore, glycerol esters of naproxen are known, having been disclosed in Belgian Patent Specification No. 903,569, published Feb. 17, 1986, by Rainoldi, and U.S. Pat. No. 3,686,238, to Zaffaroni, issued Aug. 22, 1972, the disclosure of both these publications being incorporated herein by reference in their entirety. Esters of naproxen having two chiral centers in the alcohol portion of the ester are known for use for optical resolution of naproxen and are said to have pharmacological activity, as described in European Patent Application Publication No. 158,255, published Oct. 16, 1985, by Giordano et al. There is no disclosure of topical application of these compounds.

Finally, European Patent Application Publication No. 112,130, published June 27, 1984, by Ladkani et al., discloses ethoxy-carbonyloxy ethyl esters of NSAI substances having a carboxylic acid function. These compounds are said to be prodrugs of the corresponding NSAI substances, and are generally said to be readily absorbed from the digestive tract and through skin following topical application. This publication discloses the ethoxy-carbonyloxy ethyl ester of naproxen. There is no disclosure of this ester of naproxen being formulated into a form suitable for topical application; being more or less readily absorbed through skin when applied as a diastereomeric mixture; or being applied topically to skin.

Notwithstanding the great effort already put forth to identify NSAI drugs, particularly with regard to naproxen derivatives, there remains a continuing need to identify new compounds and compositions which are effective for treating inflammation and inflammatory diseases such as rheumatoid arthritis and osteoarthritis. It is accordingly an object of the present invention to provide compounds and diastereomeric mixtures of compounds which are effective anti-inflammatory agents, as well as pharmaceutical compositions (especially compositions suitable for topical application) containing these compounds and diastereomeric mixtures. Another object of the present invention is to provide compounds and diastereomeric mixtures which are easy to synthesize, formulate, and administer. It is a further object of the present invention to provide methods for treating diseases characterized by inflammation. It is also an object of the present invention to provide compounds which are useful as anti-inflammatory agents, analgesic agents, and/or antipyretic agents. An additional object is to provide compounds and compositions which are readily absorbed, especially through the skin following topical application.

These and other objects will become readily apparent from the detailed description which follows.

All percentages and ratios used herein are by weight unless otherwise specified.

SUMMARY OF THE INVENTION

The present invention relates to specific 2-naphthyl-containing ester compounds, especially naproxen ester and naproxol ester compounds, having two or more chiral centers. These compounds are effective as anti-inflammatory agents, analgesic agents, and/or antipyretic agents, and are readily absorbed as the diastereomeric mixture, especially through the skin following topical application. These compounds comprise the general structures:

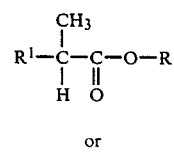

or

-continued

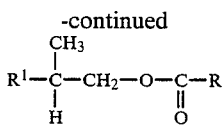

wherein $R^1$ is a 2-naphthyl residue of a naproxen-like compound having anti-inflammatory or analgesic activity; R is a $C_4$–$C_7$ unsubstituted alkyl group having at least one chiral center or a $C_1$–$C_7$ substituted alkyl group having at least one chiral center wherein the substituents are independently selected from halogen, —$OR^2$, —$SR^2$, —$NHR^2$, —$N(R^2)_2$, or combinations thereof; and each $R^2$ is independently selected from unsubstituted alkyl groups having from about 1 to about 5 carbon atoms.

The present invention further relates to diastereomeric mixtures of the ester compounds having the general formula described hereinbefore.

The present invention also relates to pharmaceutical compositions, especially compositions suitable for topical application. These pharmaceutical compositions comprise a diastereomeric mixture of the ester compounds of the present invention and a pharmaceutically-acceptable carrier, especially a carrier suitable for topical application.

Finally, the present invention relates to methods for treating diseases characterized by inflammation, such as rheumatoid arthritis and osteoarthritis, in humans or lower animals. Such methods comprise administering (especially topically to skin) to a human or lower animal in need of such treatment a safe and effective amount of a diastereomeric mixture or pharmaceutical composition of the present invention.

DETAILED DESCRIPTION OF THE INVENTION

Anti-Inflammatory Agents

The compounds useful in the present invention are specific 2-naphthyl-containing ester compounds, especially naproxen ester or naproxol ester compounds, having two or more chiral centers. The compounds are useful as anti-inflammatory agents, analgesic agents, and/or antipyretic agents. They are readily absorbed, especially through the skin following topical application, as their diastereomeric mixture.

The compounds of the present invention comprise the general structures:

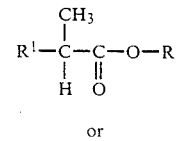

or

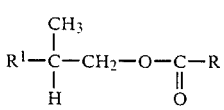

wherein $R^1$ is a 2-naphthyl residue of a naproxen-like compound having anti-inflammatory or analgesic activity; R is a $C_4$–$C_7$ unsubstituted alkyl group having at least one chiral center or a $C_1$–$C_7$ substituted alkyl group having at least one chiral center wherein the substituents are independently selected from halogen, —$OR^2$, —$SR^2$, —$NHR^2$, —$N(R^2)_2$, or combinations thereof; and each $R^2$ is independently selected from unsubstituted alkyl groups having from about 1 to about 5 carbon atoms. The term "2-naphthyl residue of a naproxen-like compound", as used herein, means the naphthyl ring structure portion of a substituted or unsubstituted 2-naphthyl propionic acid compound, (e.g., naproxen) which demonstrates anti-inflammatory and/or analgesic activity. Such 2-naphthyl propionic acid compounds are known, having been disclosed for example in U.S. Pat. No. 3,686,238, to Zaffaroni, issued Aug. 22, 1972; U.S. Pat. No. 3,637,767 to Alvarez, issued Jan. 25, 1972; U.S. Pat. No. 3,896,157, to Fried et al., issued July 22, 1975; and Harrison et al., "Non-steroidal Anti-inflammatory Agents I. 6-Substituted 2-Naphthyl-acetic Acids," *J. Med. Chem.*, 13, pages 203–205 (1970); the disclosures of these publications being incorporated herein by reference in their entirety. Preferred $R^1$ is a 6-methoxy-2-naphthyl moiety.

The R moiety is a $C_4$–$C_7$ unsubstituted alkyl group having at least one chiral center or a $C_1$–$C_7$ substituted alkyl group having at least one chiral center. Preferred R groups contain only one chiral center. The term "alkyl", as used herein, means carbon-containing chains which may be straight, branched, or cyclic; and which may be saturated, monounsaturated (i.e., one double or triple bond in the chain), or polyunsaturated (e.g., two double bonds in the chain; two triple bonds in the chain; one double and one triple bond in the chain).

The R alkyl groups may be substituted or, preferably, unsubstituted. Substituents are selected from the group consisting of halogen, —$OR^2$, —$SR^2$, —$NHR^2$, and —$N(R^2)_2$, wherein $R^2$ is an unsubstituted alkyl group having from about 1 to about 5 carbon atoms (especially methyl and ethyl). It is preferred that substituted alkyl groups be $C_2$–$C_7$ mono-substituted alkyl group. More preferred R groups are unsubstituted, saturated alkyl groups having from about 4 to about 7 carbon atoms. Examples of R groups include 2-butyl, 2-pentyl, 2-methyl-1-butyl, 2-hexyl, 3-hexyl, 2-methyl-1-pentyl, 3-methyl-1-pentyl, 2-heptyl, 3-heptyl, 2-methyl-1-cyclopropyl, 2-methyl-1-cyclopentyl, 2-but-3-enyl, 1-methoxy-1-ethyl, 1-methoxy-2-propyl, 1,3-dimethoxy-2-butyl, 1-(N,N-dimethylamino)-2-propyl, 1-(N-methylamino)-3-butyl, 1-thiomethyl-1-ethyl, and 1-(thiomethyl)-3-butyl. Preferred R groups are 2-butyl, and 2-pentyl. The most preferred R group is 2-butyl.

Preferred compounds of the present invention have the structures:

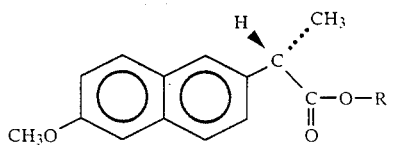

or

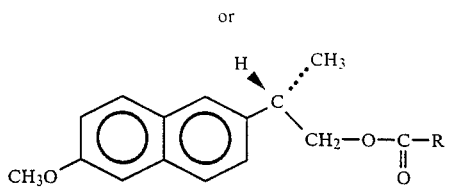

wherein R is as described hereinbefore.

Compounds of the present invention include, for example: (S)-naproxen-(S)-2-butyl ester; (S)-naproxen-(R)-2-butyl ester; (R)-naproxen-(S)-2-butyl ester; (R)- naproxen-(R)-2-butyl ester; (S)-naproxen-(S)-2-pentyl ester; (S)-naproxen-(R)-2-pentyl ester; (S)-naproxen-(S)-2-hexyl ester; (S)-naproxen-(R)-2-hexyl ester; (S)-naproxen-(S)-1-methoxy-2-propyl ester; (S)-naproxen-(R)-1-methoxy-2-propyl ester; (S)-5-bromo-naproxen-(S)-1-(N,N-dimethylamino)-2-propyl ester; (S)-5-bromo-naproxen-(R)-1-(N,N-dimethylamino)-2-propyl ester; (S)-naproxol-(R)-2-methyl butyrate; (S)-naproxol-(S)-2-methyl butyrate; (R)-naproxol-(R)-2-methyl butyrate; (R)-naproxol-(S)-2-methyl butyrate; (S)-naproxol-(R)-2-methyl pentanoate; (S)-naproxol-(S)-2-methyl pentanoate; (S)-naproxol-(R)-2-methyl-3-methoxy propanoate; (S)-naproxol-(S)-2-methyl-3-methoxy propanoate; (S)-naproxol-(R)-2-methyl-3-chloro propanoate; (S)-naproxol-(S)-2-methyl-3-chloro propanoate; (S)-naproxol-(R)-2-methyl-3-methoxy propanoate; (S)-naproxol-(S)-2-methyl-3-methoxy propanoate; (S)-5-bromo-naproxol-(R)-2-methyl butyrate; and (S)-5-bromo-naproxol-(S)-2-methyl butyrate.

Preferred compounds of the present invention include: (S)-naproxen-(S)-2-butyl ester; (S)-naproxen-(R)-2-butyl ester; (S)-naproxen-(S)-2-pentyl ester; (S)-naproxen-(R)-2-pentyl ester; (S)-naproxol-(R)-2-methyl butyrate; (S)-naproxol-(S)-2-methylbutyrate; (S)-naproxol-(R)-2-methyl pentanoate; and (S)-naproxol-(S)-2-methyl pentanoate.

Most preferred compounds of the present invention are: (S)-naproxen-(S)-2-butyl ester; (S)-naproxen-(R)-2-butyl ester; (S)-naproxol-(R)-2-methyl butyrate; and (S)-naproxol-(S)-2-methyl butyrate.

For use in the compositions and methods of the present invention, the compounds of the present invention are utilized as diastereomeric mixtures. Preferred diastereomeric mixtures are those wherein the 2-naphthyl-containing portion of the compound is only one enantiomer (e.g., for a naproxen-derived ester, this is the "S" absolute stereochemical configuration), and the R moiety portion of the compound utilized is a racemic mixture (i.e., both the "R" and "S" absolute stereochemical configurations; as described more fully in Morrison and Boyd, *Organic Chemistry*, Third Edition (Allyn and Bacon, Inc., Boston; 1973), Chapters 4 and 7, pp. 115 and 225). It is preferred that each diastereomer have two chiral centers and that the diastereomers of the diastereomeric mixture be present in amounts within the range of from about 2:1 to about 1:2, and most preferably in about equal amounts to each other (i.e., a 1:1 mixture of diastereomers).

Examples of such diastereomeric mixtures are: (S)-naproxen-(S)-2-butyl ester and (S)-naproxen-(R)-2-butyl ester; (R)-naproxen-(S)-2-butyl ester and (R)-naproxen-(R)-2-butyl ester; (S)-naproxen-(S)-2-pentyl ester and (S)-naproxen(R)-2-pentyl ester; (S)-naproxen-(S)-2-hexyl ester and (S)-naproxen-(R)-2-hexyl ester; (S)-naproxen-(S)-1-methoxy-2-propyl ester and (S)-naproxen-(R)-1-methoxy-2-propyl ester; (S)-5-bromo-naproxen-(S)-1-(N,N-dimethylamino)-2-propyl ester and (S)-5-bromo-naproxen-(R)-1-(N,N-dimethylamino)-2-propyl ester; (S)-naproxol-(R)-2-methyl butyrate and (S)-naproxol-(S)-2-methyl butyrate; (R)-naproxol-(R)-2-methyl butyrate and (R)-naproxol-(S)-2-methyl butyrate; (S)-naproxol-(R)-2-methyl pentanoate and (S)-naproxol-(S)-2-methyl pentanoate; (S)-naproxol-(R)-2-methyl-3-methoxy propanoate and (S)-naproxol-(S)-2-methyl-3-methoxy propanoate; and (S)-naproxol-(R)-2-methyl-3-chloro propanoate and (S)-naproxol-(S)-2-methyl-3-chloro propanoate; (S)-naproxol-(R)-2-methyl-3-methoxy propanoate and (S)-naproxol-(S)-2-methyl-3-methoxy propanoate; and (S)-5-bromo-naproxol-(R)-2-methyl butyrate and (S)-5-bromo-naproxol-(S)-2-methyl butyrate.

Preferred diastereomeric mixtures are: (S)-naproxen-(S)-2-butyl ester and (S)-naproxen-(R)-2-butyl ester; (S)-naproxen-(S)-2-pentyl ester and (S)-naproxen-(R)-2-pentyl ester; (S)-naproxol-(R)-2-methyl butyrate and (S)-naproxol-(S)-2-methyl butyrate; and (S)-naproxol-(R)-2-methyl pentanoate and (S)-naproxol-(S)-2-methyl pentanoate.

Most preferred diastereomeric mixtures are: (S)-naproxen-(S)-2-butyl ester and (S)-naproxen-(R)-2-butyl ester; and (S)-naproxol-(R)-2-methyl butyrate and (S)-naproxol-(S)-2-methyl butyrate.

In order to determine and assess pharmacological activity, testing of these compounds in animals is carried out using various assays known to those skilled in the art. Thus, the anti-inflammatory activity of the compounds can be conveniently demonstrated using an assay designed to test the ability of these compounds to antagonize the local edema which is characteristic of the inflammatory response. Examples of such known tests include the carrageenan rat edema test, the oxazolone-induced inflamed mouse ear test, and the arachidonic acid-induced inflamed mouse ear test. Antipyretic activity may be tested using art-known rat models, and analgesic activity may be tested in art-known models such as the acetylcholine model in mice, the Randall-Selitto model in rats, and the hot-plate test in mice. Another useful art-known test is the adjuvant arthritis test which is a useful model for assessing anti-inflammatory activity and antiresorptive activity in a chronic, rather than acute, model. Certain tests for pharmacological activity are also described in more detail in the Examples provided hereinafter.

The compounds of the present invention are prepared from commercially-available materials or readily synthesized materials by simple esterification techniques. The synthesis of naproxen and/or naproxol, and related 2-naphthyl-containing compounds, are disclosed, for example, in Harrison et al., "Nonsteroidal Anti-Inflammatory Agents. I. 6-Substituted 2-Naphthylacetic Acids", *J. Med. Chem.*, 13, pages 203–205 (1970); U.S. Pat. No. 4,395,571, to Dvorak, issued July 26, 1983; European Patent Application Publication No. 158,255, published Oct. 16, 1985, by Giordano et al.; U.S. Pat. No. 3,792,167, to Fried et al., issued Feb. 12, 1974; and U.S. Pat. No. 3,641,161, to Fried et al., issued Feb. 8, 1972; the disclosures of these patents and publications being incorporated herein by reference in their entirety. Representative procedures for synthesizing compounds and diastereomeric mixtures of the present invention are provided in the Examples hereinafter.

As noted hereinbefore, a large number of naproxen derivatives and other 2-naphthyl-containing compounds have been prepared and tested for pharmacological activity. Surprisingly, however, the compounds of the present invention are absorbed more readily as their diastereomeric mixture (especially through skin upon topical application) than naproxen or derivatives having the same number of carbon atoms but not a diastereomeric mixture. As a result of this greater bioavailability (especially topical bioavailability), the compounds of the present invention are therefore easy to formulate into forms which utilize lesser amounts or lesser concentrations of compound to get an effective dose.

The diastereomeric mixtures of the present invention typically comprises from 0.1% to 99.9% by weight of the pharmaceutical compositions of the present invention, preferably from about 0.1% to about 75%, and most preferably from about 1% to about 50%.

Pharmaceutically-Acceptable Carrier

In addition to the anti-inflammatory agent as described hereinbefore, the pharmaceutial compositions of the present invention essentially contain a pharmaceutically-acceptable carrier, especially a pharmaceutically-acceptable carrier suitable for topical dose forms. The term "pharmaceutically-acceptable carrier", as used herein, means one or more compatible solid or liquid filler diluents or encapsulating substances which are suitable for administration to a human or lower animal. The term "compatible", as used herein, means that the components of the pharmaceutical composition are capable of being commingled with the anti-inflammatory agent, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated. Some examples of substances which can serve as pharmaceutically-acceptable carriers are sugars such as lactose, glucose, and sucrose; starches such as cornstarch and potato starch; cellulose and its derivatives such as sodium carboxymethylcellulose; ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil, and oil of theobroma; polyols such as propylene glycol, glycerine, sorbitol, mannitol, and polyethylene glycol; agar; alginic acid; pyrogen-free water; isotonic saline; and phosphate buffer solutions, as well as other non-toxic compatible substitutes used in pharmaceutical formulations. Wetting agents and lubricants such as sodium lauryl sulfate, as well as coloring agents, flavoring agents, excipients, tableting agents, stabilizers, antioxidants, and preservatives, can also be present. Other compatible pharmaceutical additives and actives, (e.g., other NSAI drugs; pain killers; muscle relaxant; counter irritants) may be included in the pharmaceutically-acceptable carrier for use in the compositions of the present invention.

The choice of a pharmaceutically-acceptable carrier to be used in conjunction with the anti-inflammatory agents of the present composition is basically determined by the way the compound is to be administered. If the compound is to be administered orally, the preferred unit dosage form is tablets, capsules, and the like, comprising a safe and effective amount of the anti-inflammatory compound of the present invention. Pharmaceutically-acceptable carriers for the preferred topical application forms include those suitable for use in creams, gels, tapes, and the like. Pharmaceutically-acceptable carriers suitable for topical dose forms will depend on secondary considerations like cost, shelf stability, and cosmetic aesthetics, which are not critical for the purposes of the present invention, and can be made without difficulty by a person skilled in the art.

Topical dose forms of the compositions of the present invention include lotions, creams, ointments, solutions, gels, solids and patches. These topical compositions comprise a safe and effective amount, usually from about 0.1% to about 75%, and preferably from about 1% to about 50%, of the compound of the present invention. Pharmaceutically-acceptable carriers suitable for topical dose forms to administer these compounds preferably remain in place on the skin as a continuous film and resist being washed off easily by perspiration or by immersion in water. Generally, the pharmaceutically-acceptable carrier suitable for topical dose forms is either organic in nature or an aqueous emulsion, and is capable of having the anti-inflammatory agent dispersed or dissolved therein. The carrier may include pharmaceutically-acceptable emollients, skin penetration enhancers, coloring agents, fragrances, emulsifiers, thickening agents, and solvents. A more detailed description of topical dose forms, and pharmaceutically-acceptable carriers suitable for topical dose forms, follows:

1. Lotions

The lotions can comprise an effective amount (preferably from about 0.1% to about 75%) of the compound of the present invention; from 1% to 25%, preferably from 3% to 15%, of an emollient; the balance being water, a $C_2$ or $C_3$ alcohol, or a mixture of water and the alcohol. Several emollients are known. Examples of such emollients are as follows:

a. Hydrocarbon oils and waxes. Examples are mineral oil, petrolatum, paraffin, ceresin, ozokerite, microcrystalline wax, polyethylene, and perhydrosqualene.

b. Silicone oils, such as dimethylpolysiloxanes, methylphenylpolysiloxanes, water-soluble and alcohol-soluble silicone-glycol copolymers.

c. Triglyceride fats and oils such as those derived from vegetable, animal and marine sources. Examples include castor oil, safflower oil, cottonseed oil, corn oil, olive oil, cod liver oil, almond oil, avocado oil, palm oil, sesame oil, soybean oil, and cocoa butter.

d. Acetoglyceride esters, such as acetylated monoglycerides.

e. Ethoxylated glycerides, such as ethoxylated glyceryl monostearate.

f. Alkyl esters of fatty acids. Methyl, isopropyl and butyl esters of $C_{10}$-$C_{20}$ fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

g. Alkenyl esters of fatty acids having 10 to 20 carbon atoms. Examples thereof include oleyl myristate, oleyl stearate, and oleyl oleate.

h. Fatty acids having 9 to 22 carbon atoms. Suitable examples include pelargonic, lauric, myristic, palmitic, stearic, isostearic, hydroxystearic, oleic, linoleic, ricinoleic, arachidonic, behenic, and erucic acids.

i. Fatty alcohols having 10 to 22 carbon atoms. Lauryl, myristyl, cetyl, hexadecyl, stearyl, isostearyl, hydroxystearyl, oleyl, ricinoleyl, behenyl, erucyl, and 2-octyl dodecyl alcohols are examples of satisfactory fatty alcohols.

j. Fatty alcohol ethers. Ethoxylated fatty alcohols of 10 to 20 carbon atoms include the lauryl, cetyl, stearyl, isostearyl, and oleyl alcohols having attached thereto from 1 to 50 ethylene oxide groups or 1 to 50 propylene oxide groups, or a mixture thereof.

k. Ether-esters such as fatty acid esters of ethoxylated fatty alcohols.

l. Lanolin and derivatives. Lanolin, lanolin oil, lanolin wax, lanolin alcohols, lanolin fatty acids, isopropyl lanolate, ethoxylated lanolin, ethoxylated lanolin alcohols, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

m. Polyhydric alcohols and polyether derivatives. Propylene glycol, dipropylene glycol, polypropylene glycol (M.W. 2000–4000), polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol (MW. 200–6000), methoxy polyethylene glycols 350, 550, 750, 2000, 5000, poly-[ethylene oxide]homopolymers (M.W. 100,000–5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol) $C_{15}$–$C_{18}$ vicinal glycol, and polyoxypropylene derivatives of trimethylolpropane are examples thereof.

n. Polyhydric alcohol esters. Ethylene glycol mono- and di-fatty acid esters, diethylene glycol mono- and di-fatty esters, polyethylene glycol (M.W. 200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

o. Wax esters such as beeswax, spermaceti, myristyl myristate, stearyl stearate.

p. Beeswax derivatives, e.g., polyoxyethylene sorbital beeswax. These are reaction products of beeswax with ethoxylated sorbitol of varying ethylene oxide content, forming a mixture of ether-esters.

q. Vegetable waxes including carnauba and candelilla waxes.

r. Phospholipids such as lecithin and derivatives.

s. Sterols. Cholesterol, cholesterol fatty acid esters, and ethoxylated cholesterol are examples thereof.

t. Amides such as fatty acid amides, ethoxylated fatty acid amides, solid fatty acid alkanolamides. The lotions further comprise from 1% to 10%, preferably from 2% to 5%, of an emulsifier. The emulsifiers can be nonionic, anionic or cationic. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxide, mono- and di-fatty acid esters of ethylene glycol wherein the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include the fatty acid soaps, e.g. sodium, potassium and triethanolamine soaps, wherein the fatty acid moiety contains from 10 to 20 carbon atoms. Other suitable anionic emulsifiers include the alkali metal, ammonium or substituted ammonium alkyl sufates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pyridinium compounds. Certain emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably the compound of the present invention is dissolved in the mixture. Conventional optional components can be included. One such additive is a thickening agent at a level from 1% to 10% of the composition. Examples of suitable thickening agents include: cross-linked carboxypolymethylene polymers, ethyl cellulose, polyethylene glycols, gum tragacanth, gum karaya, xanthan gums and bentonite.

2. Creams

Compositions of this invention also can be formulated in a cream form. The creams comprise an effective amount (preferably from about 0.1% to about 75%) of the compound of the present invention; from 5% to 50%, preferably from 10% to 25%, of an emollient; the balance being water. The emollients above described can also be used in the cream compositions. Optionally the cream form contains a suitable emulsifier, as previously described. When an emulsifier is included, it is in the composition at a level from 3% to 50%, preferably from 5% to 20%.

3. Solutions

The compositions of this invention can be also formulated in a solution form. The solution form comprises an effective amount (preferably from about 0.1% to about 75%) of the compound of the present invention; the balance being water and/or a suitable organic solvent. Suitable organic materials useful as the solvent or a part of a solvent system are as follows: propylene glycol, polyethylene glycol (M.W. 200–600), polypropylene glycol (M.W. 425–2025), glycerine, sorbitol esters, 1,2,6-hexanetriol, ethanol, isopropanol, diethyl tartrate, butanediol, and mixtures thereof. Such solvent systems can also contain water.

These compositions in the solution form can be applied to the skin as is, or else can be formulated into an aerosol and applied to the skin as a spray-on. The aerosol compositions further comprise from 25% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used at a level sufficient to expel the contents of the container.

4. Gels

Compositions herein can be formulated into a gel form by simply admixing a suitable thickening agent to the previously described solution compositions. Examples of suitable thickening agents have been previously described with respect to the lotions.

The gelled compositions comprise an effective amount (preferably from about 0.1% to about 75%) of the compound of the present invention; from 5% to 75%, preferably from 10% to 50%, of an organic solvent as previously described; from 0.5% to 20%, preferably from 1% to 10% of the thickening agent; the balance being water.

5. Solids

The compositions of this invention can also be formulated into a solid form. Such forms have use as a stick-type composition intended for application to the lips or other parts of the body. Such compositions comprise an effective amount (preferably from about 0.1% to about 75%) of the compound of the present invention and from 50% to 98%, preferably from 60% to 90%, of the previously described emollients. This composition can further comprise from 1% to 20%, preferably from 5% to 15%, of a suitable thickening agent, and optionally emulsifiers and water. Thickening agents previously described with respect to lotions are suitable herein.

6. Patches

Compositions herein can be further formulated into a patch form suitable for transdermal delivery of the compounds of the present invention. Compositions in patch form are preferred for the present invention, especially when systemic anti-inflammatory activity is desired. Compositions in patch form may be readily prepared by one skilled in the art using known patch carrier materials as described more fully in "Transdermal and Related Drug Delivery Systems", *Chemical Technology Review No.* 228 (Noyes Data Corporation, Park Ridge, N.J.; 1984; Jones, editor), especially pages 109–296, the disclosures of which are incorporated herein by reference in their entirety.

Additives commonly found in topical compositions such as preservatives, e.g., methyl and ethyl-paraben, dyes and perfumes can be included in any of the previously described topical compositions.

The preferred dosage forms for topical administration are lotions or patches comprising a safe and effective amount of the anti-inflammatory agent of the present invention. Lotions preferably comprise an anti-inflammatory agent at a concentration of from about 1 mg/ml to about 750 mg/ml, and more preferably from about 10 mg/ml to about 500 mg/ml.

The pharmaceutically-acceptable carrier employed in conjunction with the anti-inflammatory agents of the present invention is used at a concentration sufficient to provide a practical size to dosage relationship. The pharmaceutically-acceptable carriers, in total, may comprise from about 0.1% to about 99.9% by weight of the pharmaceutical compositions of the present invention, preferably from about 25% to about 99.9%, and most preferably from about 50% to about 99%.

Methods of Treating Diseases Characterized by Inflammation

Another aspect of the present invention is methods for treating diseases characterized by inflammation. Such methods comprise administering to a human or lower animal in need of such treatment a safe and effective amount of an anti-inflammatory agent described hereinbefore.

The preferred mode for administration is topical, but other known methods for administration are contemplated as well, e.g., oral and parenteral (for example, by subcutaneous injection, intramuscular injection, intra-articular injection, intravenous injection, and the like). Ocular administration and inhalation is also included. Thus, specific modes of administration include, without limitation, oral, transdermal, mucosal, sublingual, intramuscular, intravenous, intraperitoneal, and subcutaneous administration, as well as the preferred topical application.

The term "diseases characterized by inflammation", as used herein, means conditions which are known to involve inflammation, such as arthritis (e.g., rheumatoid arthritis; osteoarthritis; psoriatic arthritis; juvenile arthritis; Reiter's syndrome; infectous arthritis; ankylosing spondylitis; systemic lupus erythematosus; and gout), as well as the presence of inflammation whether or not it is associated with an identifiable disease. Diseases characterized by inflammation further include inflammation of the gastrointestinal tract, including the oral cavity (e.g., inflammation associated with gingivitis or periodontal disease) and bowels (e.g., inflammation associated with inflammatory Bowel Disease); inflammation associated with dermatological diseases (e.g., psoriasis); and inflammation associated with the respiratory tract (e.g., pulmonary inflammation).

The phrase "safe and effective amount", as used herein, means an amount of a compound or composition high enough to significantly positively modify the condition to be treated, but low enough to avoid serious side effects (at a reasonable benefit/risk ratio), within the scope of sound medical judgment. The safe and effective amount of the anti-inflammatory agent will vary with the particular condition being treated, the age and physical condition of the patient being treated, the severity of the condition, the duration of the treatment, the nature of concurrent therapy, the specific anti-inflammatory agent employed, the particular pharmaceutically-acceptable carrier utilized, and like factors within the knowledge and expertise of the attending physician. However, single dosages can range from about 100 mg to about 2000 mg. Preferred single dosages are from about 250 mg to about 1000 mg. Up to about 4 single dosages per day may be administered.

Topical administration can be used to reduce inflammation through directly laying on or spreading a safe and effective amount of the compound or composition of the present invention on epidermal or epithelial tissue, including outer skin and oral, gingival, and nasal tissue. The amount of the pharmaceutical composition to be topically administered may vary from about 0.1 mg/cm$^2$ to 10 mg/cm$^2$, and if a patch is worn over the affected area possibly higher concentrations, depending upon such factors as the sensitivity, type and location of tissue to be treated, the composition and carrier (if any) to be administered, and the particular compound to be administered as well as the particular disorder to be treated and the extent to which systemic (as distinguished from local) effects are desired. The extent of systemic anti-inflammatory activity also depends upon such factors as the amount of compound, the area of tissue to be covered, and the ability of the compound to penetrate the skin tissue.

The following Examples further describe and demonstrate embodiments within the scope of the present invention. The Examples are given solely for the purpose of illustration, and are not to be construed as limitations of the present invention since many variations thereof are possible without departing from its spirit and scope.

EXAMPLE I

Synthesis of a Diastereomeric Mixture of the Sec-Butanol Ester of Naproxen

Thionyl chloride (6.08 ml; 0.084 mole; Baker reagent, redistilled) is added dropwise over 20 minutes to a suspension of S(+)-naproxen (6.45 grams; 0.028 mole; Sigma Chemical Co.) in 120 ml of anhydrous diethyl ether and 15 ul N,N-dimethylformamide. After two hours of refluxing, a clear solution results. The solvent is removed under reduced pressure and the resulting solid is devolatilized for 5 hours (1 mm Hg and ambient temperature). This naproxen acid chloride is used for ester preparations without further purification.

The S(+)-naproxen acid chloride (6.45 grams; 0.028 mole) is dissolved in 120 ml of dichloromethane and cooled in an ice bath. 2-Butanol (racemic mixture; 2.57 ml; 0.028 mole; Aldrich Chemical Co.) and pyridine (2.14 ml) in dichloromethane (20 ml) is added to the stirred solution over 20 minutes. After stirring 16 hours at ambient temperature, the solution is poured into ice water and washed successively with 1N aqueous hydrochloric acid, water, and 10% sodium carbonate. The solvent is then dried (anhydrous sodium sulfate) and the solvent removed to give a yellow oil. Purification by flash chromatography on silica gel (hexane/ethyl acetate, 96:4) provides 7.43 grams (93%) of colorless oil product (S)-naproxen-(S,R)-2-butyl ester.

HPLC (150×4.6 mm i.d. Zorbax ODS column eluted at 2.0 ml/minute with 650:349:1 $CH_3CN:H_2O:HOAc$) indicates the presence of a diastereomeric mixture of S,R diastereomer and S,S diastereomer in a ratio of 49:51. $[\alpha]D$ (25° C.)= +22° (C, 3.2, $CHCl_3$). $^1H$-NMR ($CDCl_3$): 0.6–1.75(superimposed m), 1.09 (d, J=7) 1.21 (d, J=7), 1.58 (d, J=8), 3.86 (q, J=7), 3.95 (s), 4.92 (q of t, J=7,7), 7.07–7.92 ppm (m).

EXAMPLE II

Synthesis of a Diastereomeric Mixture of Naproxol 2-Methyl Butyrate

A solution of 2-methyl butyryl chloride (5.46 ml, 0.0455 mole; racemic mixture; Eastman Kodak) in 50 ml of dry dichloromethane is added over 15 minutes to a stirred solution of 7.19 gm (0.0333 mole) of S(−)-2-(6-methoxynapth-2-yl)-1-propanol ("naproxol", which is prepared as described in *J. Med. Chem.*, 13, 203 (1970), $[\alpha]D$ (25° C.)= −18.6° (C, 1.5, $CHCl_3$)) and 2.69 ml (0.0333 mole) of dry pyridine in 90 ml of dichloromethane maintained at 0°–3° C. in an ice bath and under a nitrogen atmosphere. After 16 hours at ambient temperature, the reaction is washed successively with water, 0.1N aqueous hydrochloric acid, water, 10% sodium carbonate, water, and brine. Removal of solvent under vacuum from the dried solution (anhydrous sodium sulfate) gives the product (S)-naproxol-(R,S)-2-methyl butyrate as an oil. Purification by flash chromatography on silica gel (hexane/ethyl acetate, 95:5) gives 8.38 g (84%) of colorless liquid product. $[\alpha]D$ (25° C.)= −16.0° (C, 3.0, $CHCl_3$). $^1H$-NMR ($CDCl_3$): 0.6–1.90(superimposed m), 0.90 (d, J=7), 1.09 (d, J=7), 2.35 (septet, J=7), 3.26 (sextet, J=7), 3.94 (s), 4.29 (d, J=7), and 7.03–7.87 ppm (m).

EXAMPLE III

Procedure for Skin Penetration Measurements (Maximum Flux Experiments)

Human skin is obtained from cadavers by dermatoming after the hair has been clipped and the skin washed. The skin thickness is approximately 0.25 mm and the samples are stored at −80° C. Prior to use, the samples are rapidly thawed and the glycerol used in the storage process is removed by washing in distilled water.

The skin samples are mounted in 5-mm diameter glass diffusion cells (E. W. Merritt and E. R. Cooper, "Diffusion Apparatus for Skin Penetration", *J. Controlled Release*, 1(2), 161–162 (1984)) with closed tops and a magnetic stirring bar in the lower compartment. The diffusion cells (nonjacketed) are placed in an aluminum block regulated at 37° C. with a stirring magnet below the block. The dermis is bathed in 4 ml of a 1:1 (v:v) solution of ethanol and distilled water containing 0.02% sodium azide to inhibit microbial growth. The ethanol is used in order to ensure the solubility of the compounds in the receptor phase and to minimize the effect of unstirred aqueous layers in the epidermis and remaining dermis.

After an overnight equilibration, the receptor solution is exchanged with fresh solution and the stratum corneum is dosed with 200 ul of a saturated solution of the test compound in propylene glycol. The receptor solution is removed for the penetration assay after elapsed times of 6, 24, 48, and 72 hours and replaced with a fresh 4 ml volume.

Steady state flux is often not achieved until the 24–48 hour time interval. The reported value of maximum flux (Jm) is the flux from 48–72 hours. In no case are the vehicles more than 10% depleted by the end of the experiment.

The diasteriomeric mixture of compounds of the present invention penetrate human skin substantially better than naproxen or derivatives having the same number of carbon atoms but not a diastereomeric mixture.

EXAMPLE IV

Carrageenan Rat Paw Edema Tests

Compounds of the present invention are tested for anti-inflammatory activity following subcutaneous or topical administration using the carrageenan rat paw edema test.

(a) Subcutaneous

Male Sprague-Dawley rats weighing 170–210 g are divided into 4 groups of 6 animals and fasted for 24 hours. The drug is dissolved in a solvent composed of 10 parts of ethanol, 10 parts of Polysorbate 80, and 80 parts of normal saline. One ml of the solution is injected subcutaneously into the dorsal neck area 1 hour prior to the carrageenan injection. Immediately thereafter the animals are given 5 ml of tap water by gavage. Paw volumes are determined with a mercury displacement device equipped with a transducer and digitizer. One hour after receiving the drug, 50 ul of 1% (w/w) carrageenan (Viscarin, Marine Colloids, Inc.) in normal saline are injected into the ventral left rear paw of each animal. Four hours later, paw volumes are again measured.

(b) Topical

Male Sprague-Dawley rats weighing 170–210 g are divided into 4 groups of 6 animals and fasted during the course of the experiment. The backs of the animals are clipped with a small animal clippers and the 200 mg of the topical preparation applied to a 20 cm² area (4×5 cm). The drugs are dissolved at a 5% concentration in a 1:1 mixture of propylene glycol and ethanol. Applications are made 19.5 and 2.5 hours prior to injection of the 1% carrageenan solution. A plastic Elizabethan collar is fitted around the neck to prevent ingestion of the topical drug. Two hours after the last application the collars are removed and the animals are given 5 ml of water by gavage. Following injection of carrageenan, all procedures are the same as for the subcutaneous dose.

(c) Calculations and Statistical Methods

The results are expressed as percent inhibition of the mean paw volume of the test group relative to the control group according to the formula:

$$(C - T_{a...n}) \times 100/C = \text{Percent Inhibition}$$

where: C is the average difference in paw volume before and after carrageenan-induced swelling, and $T_{a...n}$ is the difference in paw volume swelling in treated animal (a ... n). Statistical significance is determined by a one-way analysis of variance of the carrageenan-treated paw volume differences. Generally, the diastereomeric mixtures of the present invention demonstrate anti-inflammatory activity similar to naproxen.

EXAMPLE V

Oxazolone-Induced Inflammed Mouse Ear Test

Adult male Cox ICR mice, 20–28 g, are sensitized by application of 3% oxazolone in olive oil to the clipped abdomen of each animal. One week later the animals are challenged on the inner aspects of the left ear with 3% oxazolone in acetone. At the same time 25 ul of the drug solution is applied to the same ear. Six hours later a second application of the drug solution is made. Twenty-four hours after challenge, the animals are sacrificed and 5-mm punch biopsies are taken from each ear and weighed. Ten to twelve animals are used per group. The control group is only challenged on the left ear.

The results are expressed as percent inhibition of the swelling response compared to the control group according to the formula:

$$(C - T_{a...n}) \times 100/C = \text{Percent Inhibition}$$

where: C is the average difference between the left and right ear weights of the control group, and $T_{a...n}$ is the difference between left and right ear weights of animal (a ... n) in a treated group.

Statistical tests for signficance between groups are made using a one-way analysis of variance of the ear weight differences. Generally, the diastereomeric mixtures of the present invention demonstrate anti-inflammatory activity similar to naproxen.

EXAMPLE VI

A composition for topical administration is prepared by combining the following ingredients:

| Component | Weight % |
| --- | --- |
| Naproxol 2-Methyl Butyrate[1] | 5.0 |
| Propylene Glycol | 47.5 |

| Component | Weight % |
| --- | --- |
| Ethanol | 47.5 |

[1] A 1:1 diastereomeric mixture of the S,S and S,R diastereomers, prepared as in Example 2.

Topical application of 0.4 ml of this liquid to a 80 cm² portion of inflammed skin of a human produces anti-inflammatory activity. Similar anti-inflammatory activity is obtained when the naproxol 2-methyl butyrate is replaced with the 2-butanol ester of naproxen.

What is claimed is:

1. 2-Naphthyl-containing ester compounds having anti-inflammatory or analgesic activity comprising the general structures:

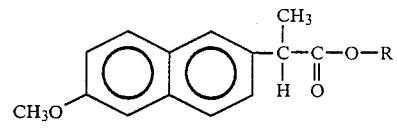

or

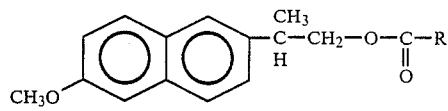

wherein R is a $C_4$–$C_7$ unsubstituted alkyl group having at least one chiral center.

2. Compounds according to claim 1, comprising the general structures:

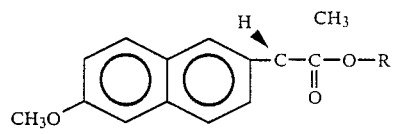

or

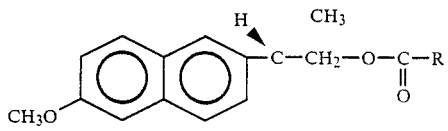

wherein R is a $C_4$–$C_7$ unsubstituted alkyl group having at least one chiral center.

3. Compounds according to claim 2, wherein R is selected from the group consisting of 2-butyl, 2-pentyl, 2-methyl-1-butyl, 2-hexyl, 3-hexyl, 2-methyl-1-pentyl, 3-methyl-1-pentyl, 2-heptyl, 3-heptyl, 2-methyl-1-cyclopropyl, 2-methyl-1-cyclopentyl and 2-but-3-enyl.

4. Compounds according to claim 3, wherein the compounds are selected from the group consisting of (S)-naproxen-(S)-2-butyl ester; (S)-naproxen-(R)-2-butyl ester; (S)-naproxen-(S)-2-pentyl ester; (S)-naproxen-(R)-2-pentyl ester; (S)-naproxol-(R)-2-methyl butyrate; (S)-naproxol-(S)-2-methyl butyrate; (S)-naproxol-(R)-2-methyl pentanoate; and (S)-naproxol-(S)-2-methyl pentanoate.

5. Compounds according to claim 4, wherein the compounds are selected from the group consisting of (S)-naproxen-(S)-2-butyl ester; (S)-naproxen-(R)-2-butyl ester; (S)-naproxol-(R)-2-methyl butyrate; and (S)-naproxol-(S)-2-methyl butyrate.

6. Diasteromeric mixtures of two or more compounds according to claim 1.

7. Diasteromeric mixtures of two or more compounds according to claim 2.

8. Diasteromeric mixtures of two or more compounds according to claim 3.

9. Diasteromeric mixtures of two or more compounds according to claim 4.

10. Diasteromeric mixtures of two or more compounds according to claim 5.

11. Pharmaceutical compositions comprising:
(a) a diastereomeric mixture according to claim 6; and
(b) a pharmaceutically-acceptable carrier suitable for topical dose forms.

12. Pharmaceutical compositions comprising:
(a) a diastereomeric mixture according to claim 7; and
(b) a pharmaceutically-acceptable carrier suitable for topical dose forms.

13. Pharmaceutical compositions comprising:
(a) a diasteromeric mixture according to claim 8; and
(b) a pharmaceutically-acceptable carrier suitable for topical dose forms.

14. Pharmaceutical compositions comprising:
(a) a diastereomeric mixture according to claim 9; and
(b) a pharmaceutically-acceptable carrier suitable for topical dose forms.

15. Pharmaceutical compositions comprising:
(a) a diastereomeric mixture according to claim 10; and
(b) a pharmaceutically-acceptable carrier suitable for topical dose forms.

16. Methods for treating diseases characterized by inflammation, said methods comprising administering to a human or lower animal in need of such treatment a safe and effective amount of a diastereomeric mixture according to claim 6.

17. Methods for treating diseases characterized by inflammation, said methods comprising administering to a human or lower animal in need of such treatment a safe and effective amount of a diastereomeric mixture according to claim 9.

18. Methods for treating diseases characterized by inflammation, said methods comprising administering to a human or lower animal in need of such treatment a safe and effective amount of a diastereomeric mixture according to claim 10.

* * * * *

UNITED STATES PATENT AND TRADEMARK OFFICE
CERTIFICATE OF CORRECTION

PATENT NO. : 4,912,248
DATED : March 27, 1990
INVENTOR(S) : Larry G. Mueller

It is certified that error appears in the above-identified patent and that said Letters Patent is hereby corrected as shown below:

Column 16, lines 26-29, " 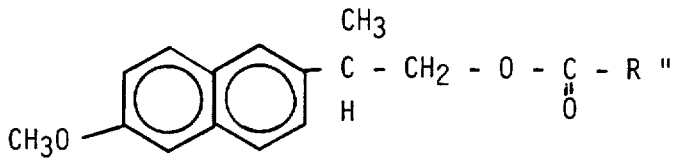 "

should read

-- 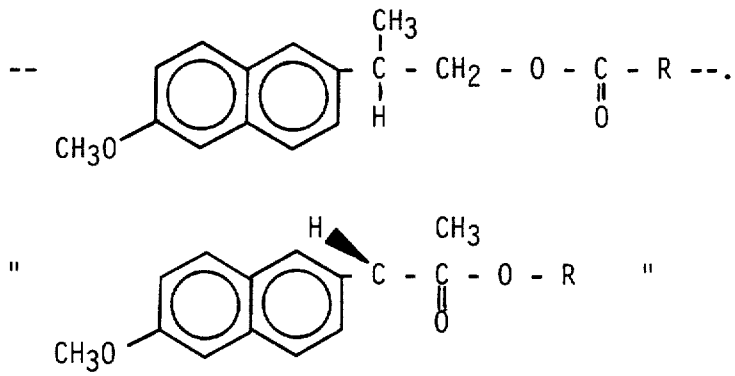 --.

Column 16, lines 36-47, " 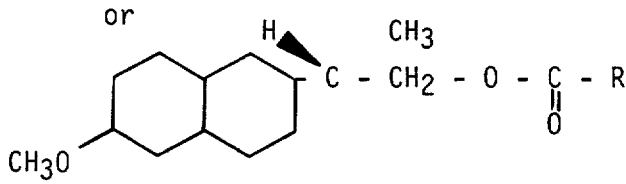 "

UNITED STATES PATENT AND TRADEMARK OFFICE
CERTIFICATE OF CORRECTION

PATENT NO. : 4,912,248

DATED : March 27, 1990

INVENTOR(S) : Larry G. Mueller

It is certified that error appears in the above—identified patent and that said Letters Patent is hereby corrected as shown below:

should read

-- 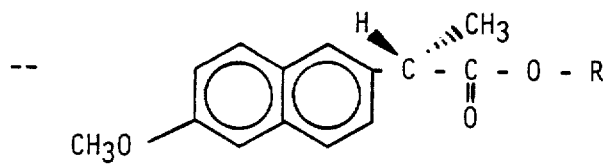

or

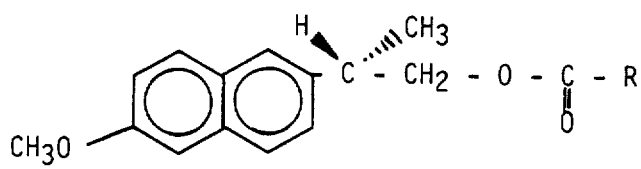 --.

Signed and Sealed this

Second Day of June, 1992

Attest:

DOUGLAS B. COMER

Attesting Officer      Acting Commissioner of Patents and Trademarks